(12) United States Patent
Casey

(10) Patent No.: US 8,790,314 B2
(45) Date of Patent: Jul. 29, 2014

(54) DRUG DELIVERY DEVICE

(75) Inventor: Bill Casey, San Diego, CA (US)

(73) Assignees: Amylin Pharmaceuticals, LLC, San Diego, CA (US); AstraZeneca Pharmaceuticals LP, Wilmington, DE (US)

( * ) Notice: Subject to any disclaimer, the term of this patent is extended or adjusted under 35 U.S.C. 154(b) by 1095 days.

(21) Appl. No.: 12/597,468

(22) PCT Filed: Apr. 25, 2008

(86) PCT No.: PCT/US2008/061666
§ 371 (c)(1),
(2), (4) Date: Mar. 30, 2010

(87) PCT Pub. No.: WO2008/134580
PCT Pub. Date: Nov. 6, 2008

(65) Prior Publication Data
US 2010/0211042 A1   Aug. 19, 2010

Related U.S. Application Data

(60) Provisional application No. 60/914,461, filed on Apr. 27, 2007.

(51) Int. Cl.
*A61M 5/24* (2006.01)
*A61M 5/32* (2006.01)

(52) U.S. Cl.
USPC .......................................... 604/200; 604/192

(58) Field of Classification Search
USPC ............. 604/506, 171, 272, 198, 187, 46, 47, 604/200
See application file for complete search history.

(56) References Cited

U.S. PATENT DOCUMENTS

| | | | |
|---|---|---|---|
| 4,900,311 A * | 2/1990 | Stern et al. | 604/198 |
| 5,015,239 A | 5/1991 | Browne | |
| 5,312,376 A * | 5/1994 | Van Heugten | 604/272 |
| 5,480,384 A | 1/1996 | Highgate | |
| 5,635,215 A | 6/1997 | Boschetti et al. | |
| 5,718,676 A * | 2/1998 | Barrett | 604/22 |
| RE38,964 E * | 1/2006 | Shillington | 604/240 |
| 2006/0129100 A1* | 6/2006 | Tal | 604/164.1 |

FOREIGN PATENT DOCUMENTS

WO   WO 94/03224 A1   2/1994
WO   WO 2008/134580 A2   11/2008

OTHER PUBLICATIONS

Written Opinion of the International Searching Authority for International Application No. PCT/US08/61666, filed Apr. 25, 2008, Written Opinion of the International Searching Authority dated Sep. 16, 2008 and mailed Sep. 22, 2008 (5 pgs.).
International Search Report for International Application No. PCT/US08/61666, filed Apr. 25, 2008, International Search Report dated Sep. 16, 2008 and mailed Sep. 22, 2008 (2 pgs.).

* cited by examiner

*Primary Examiner* — Nicholas Lucchesi
*Assistant Examiner* — Weng Lee
(74) *Attorney, Agent, or Firm* — Womble Carlyle Sandridge & Rice LLP; Mark J. Pino; Alireza Behrooz

(57) ABSTRACT

Embodiments of the invention generally provide a device and method for minimizing injection pain and preventing needle clogging during injection of a drug formulation into skin. Generally, the invention provides a device comprising a needle having a point to penetrate skin on one end, a hub having a diameter larger than that of the needle attached to the opposite end of the needle and connectable to a housing defining a chamber for receiving a formulation, and a polymer wrap attached to the hub, wherein the polymer wrap is tapered to the needle so as to pass through skin when the point is inserted into the skin, and wherein a space between the needle and the polymer wrap lies in a flow path of the formulation into the skin, such that formulation is injected through the space between the needle and the polymer wrap.

17 Claims, 3 Drawing Sheets

DRUG DELIVERY DEVICE

This application is the National Stage of International Application No. PCT/US2008/061666, filed Apr. 25, 2008, which claims the benefit of U.S. provisional application No. 60/914,461, filed Apr. 27, 2007, each of which is hereby incorporated by reference in its entirety, including all tables, figures, and claims.

BACKGROUND

Hypodermic syringes are used to inject or extract liquid solutions from body tissues. Pain experienced by patients using hypodermic syringes continues to be a problem, and is a primary cause of missed drug administrations and appointments. Smaller gauge needles have been introduced to reduce pain associated with penetrating skin surfaces with needles. However, smaller gauge needles tend to clog when being used to administer various viscous drug solutions or suspensions, including suspensions containing microspheres. Larger gauge needles do not tend to clog when being used to administer drug solutions through the skin, but cause the patient significant pain when entering the skin.

A variety of devices have been proposed for the subcutaneous administration of drug solutions. One type of device utilizes a dual-compartment syringe. One compartment of the syringe contains a diluent, and the other compartment contains a powdered drug. The sidewall of the syringe contains a groove just forward of the stopper between the chambers. As the plunger is pushed, the groove allows fluid to leak into the drug chamber. The drug and diluent are mixed by the turbulence created as the fluid from the diluent chamber enters the drug chamber, and then the injection is administered through an attached syringe. The disadvantages of this method include use of a non-custom syringe and a large needle which needs to accommodate the drug/diluent mixture, thereby causing excessive rain in the patient.

Devices which include a sheath wrapped around a syringe needle have also been previously presented. However, to the extent that the sheath may be made of a polymer, the sheath does not dilate an injection area once the needle is inserted into skin. The primary purpose of such sheaths is the protection of the needle during injection and during the withdrawal of the needle after injection. For example, a common application involves a sheath which is tightly wrapped over a steel needle. The needle is inserted into the skin, and once in place, the needle is withdrawn from the skin, leaving the sheath in a desired position within the skin. The sheath does not expand in response to depression by a plunger or in response to injection of a fluid or solution.

SUMMARY OF THE INVENTION

In one aspect the present invention provides devices for injecting a formulation into a patient. The devices have a needle having proximal and distal ends and a point to penetrate skin on the distal end. A hub is present having a diameter larger than that of the needle attached to the proximal end of the needle. The device also has a polymer wrap enveloping the needle, and a space present between the needle and the polymer wrap. The polymer wrap is tapered to the needle and passes through skin when the point is inserted into the skin. The polymer wrap has a proximal end closest to the housing and a distal end farthest from the housing. The space between the needle and the polymer wrap lies in a flow path of the formulation, which is injected through the space between the needle and the polymer wrap. The "hub" is a piece to which the needle is attached. In one embodiment the hub is the hilt of a needle. The hub can be further attached to a housing, which holds a fluid or formulation to be injected. In one embodiment the housing is a syringe to which the device is attached, and in another embodiment it is the barrel of a syringe. Thus, the hub is adapted to be connectable to the housing. Thus the hub joins the housing and the needle and polymer wrap, and provides a flow path from the housing to the distal end of the polymer wrap.

The hub of the device is connectable to a housing defining, which contains a chamber for receiving a formulation, for example the barrel of a syringe. In one embodiment the hub has a connector for connecting the hub to a housing for receiving a formulation. In one embodiment the housing is a syringe. The connector can be any mechanism for connecting the hub to the housing, for example, a threaded connector, or a quick release connector, or a connector that operates based on frictional connection between the housing and connector. In another embodiment the hub is connected by a molded connection. By a "molded connection" is meant a fusing or melding of the material of the hub and the housing to form a singular unit.

In one embodiment the diameter of the needle and at least a portion of the diameter of the hub lie in the flow path of the formulation into the skin. In one embodiment the flow path of the formulation begins in the housing and flows through the space between the needle and the polymer wrap from the proximal end of the needle towards the distal end of the needle, out of the end of the polymer wrap and into the patient receiving the formulation. The needle of the device can be of any gauge, but in one embodiment it is 30 gauge or smaller in diameter. In one embodiment the polymer wrap is attached to the needle with an adhesive. The adhesive can seal the polymer wrap so that no flow path is present between the housing and the distal end of the polymer wrap, thus sealing the device. In other embodiments channels are present leaving a flow path between the housing and the distal end of the polymer wrap. In various embodiments the polymer wrap can be made of any suitable polymer, for example, silicones, polyethylenes, polypropylenes, polystyrenes, polytetrafluoroethylenes, nylons, polyurethanes, nitrile rubbers, and polychloroprenes are all suitable polymers. In one embodiment the polymer wrap expands radially when the formulation is pushed through the space between the needle and the polymer wrap. In another embodiment of a sealed device the adhesive bond between the needle and the polymer wrap is broken when the formulation is pushed through the space between the needle and the polymer wrap, thus unsealing the device.

In another aspect the present invention provides methods for injecting a formulation into skin. The methods involve penetrating the skin with any of the devices described above, and pushing or injecting the formulation through the device such that the formulation passes through a space between the needle and the polymer wrap. In one embodiment the formulation flows from the housing towards the distal end of the needle and into the patient to whom the formulation is being administered. At least a portion of the polymer wrap can be inserted into the skin when the point of the needle penetrates the skin. The polymer wrap can expand radially when the fluid is pushed through the space between the needle and the polymer wrap. In some embodiments the fluid contains microspheres. In another embodiment the diameter of the needle and at least a portion of the diameter of the hub lie in the flow path of the fluid into the skin. In another embodiment the formulation flows from the housing into the polymer wrap causing an adhesive bond between the needle and the polymer wrap to break, thus creating a flow path from the housing to the exterior of the device.

BRIEF DESCRIPTION OF THE DRAWINGS

For a further understanding of the nature and objects of the present invention, reference should be made to the following detailed description, taken in conjunction with the accompanying drawings, in which like elements are given the same or analogous reference numbers and wherein.

DESCRIPTION OF EMBODIMENTS

Figure 1:
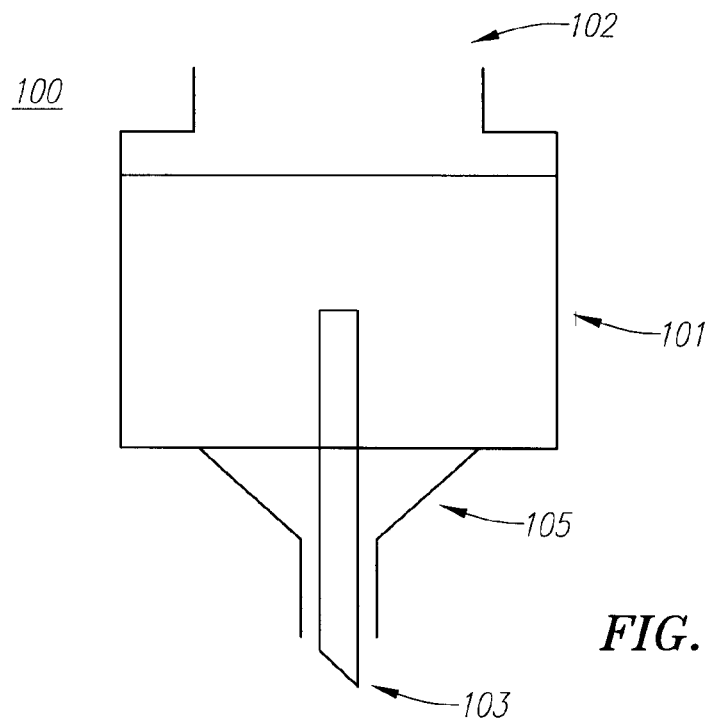
FIG. 1 exhibits the device according to one embodiment of the invention.

The words and phrases used herein should be given their ordinary and customary meaning in the art by one skilled in the art unless otherwise further defined.

Embodiments of the present invention generally provide a device and methods for injecting an active agent formulation into the skin of a mammal (e.g., a human being). In embodiments of the invention, the device comprises a needle attached to a hub. A polymer wrap can also be attached to the needle and hub, whereby channels allow a formulation to pass through the hub and through a space present between the needle and the polymer wrap. In one embodiment the polymer wrap is connected to the base of the hub. In another embodiment the polymer wrap is attached to the needle by an adhesive. When formulation passes through the polymer wrap the bond between the polymer wrap and the needle is broken, causing the polymer wrap to expand away from the surface of the needle and thereby creating space within the polymer wrap to allow formulation to pass through the polymer wrap. In some embodiments the adhesive seals the low path between the housing and the distal end of the polymer wrap (i.e., the end farthest from the housing). In other embodiments channels are present within the polymer wrap leaving a flow path between the housing and the distal end of the polymer wrap while adhesive affixes the polymer wrap to other portions of the needle. In one embodiment the housing is a syringe, having a plunger and a barrel. In one embodiment the polymer wrap splits either radially or longitudinally when the plunger of the syringe is depressed, thus allowing for a flow path from the interior of the polymer wrap to the exterior of the device (i.e., to be injected into the patient receiving the formulation). The amount of force applied to the plunger that is necessary to split the adhesive can be any appropriate amount of force. In various embodiments it is at least 5 psi, at least 10 psi, at least 15 psi, at least 20 psi, or at least 25 psi, or an amount greater than 25 psi.

Generally, in certain aspects, the needle may provide an access point through the skin of a user by puncturing the skin, while the polymer wrap may then enter the skin and allow the formulation to pass there through. Embodiments also include a housing for receiving a fluid attached to, connected to, or otherwise integrated with the hub. In various embodiments the device is detachable from the housing, or may be manufactured in a unitary manner with the housing or molded to the housing. Embodiments include various channel geometries through which fluid from the housing can be moved to the injection site. In a particular embodiment, the channels in the hub are large enough to allow all of the fluid from the housing to be administered, while being small enough to ensure that the hub does not break when the needle penetrates the skin. Fluid including a drug formulation can pass from the housing to the hub, and consequently between the needle and the polymer wrap, or both through the needle and between the needle and polymer wrap. In other embodiments the polymer wrap is secured to the needle by use of an adhesive. As formulation passes from the housing into the polymer wrap, the adhesive bond between the needle and the polymer wrap is broken, thus allowing the formulation to pass through the polymer wrap. In some embodiments the formulation exits the device through the distal end of the polymer wrap, while in other embodiments the formulation exits the device through a split or tear in the polymer wrap, which can be caused by downward pressure exerted on the plunger of a syringe.

The polymer wrap is tapered to the needle such that it passes through the plane of the skin when the needle punctures the skin. In one embodiment, the polymer wrap is tapered to the needle by means of an adhesive. After the needle and polymer wrap are inserted into the skin, formulation can be directed sub-cutaneously. As the drug formulation is injected, the lateral pressure created as the formulation passes between the polymer wrap and the needle can cause the polymer wrap to separate from the needle, and the space between the polymer wrap and needle to thereby expand. In some embodiments the expansion of space between the polymer wrap and the needle increase the injection diameter of the device, allowing a drug formulation to enter the skin with less pressure applied to the chamber. The "injection diameter" is the diameter of the opening in the skin created by the device. In some embodiments the polymer wrap splits either radially or longitudinally, or a combination thereof, during injection and increases the cross sectional area through which the drug formulation flows. In such embodiments the pressure created by injected fluid is sufficient to generate the split, with a combination of further pressure and shear causing the split to propagate.

Additional embodiments of the present invention may provide a polymer wrap affixed to the needle by an adhesive, helping maintain pressure while a formulation fills the space between the needle and polymer wrap, causing either the adhesive to separate or the polymer wrap to burst within the skin. In another embodiment of the present invention, a needle with a rounded shaft may be provided to enlarge the point of penetration into skin and thereby facilitate the entrance of the tapered polymer wrap into the skin. In yet another embodiment, a needle with a penetrating end of larger diameter than the non-penetrating end can be used to facilitate the entrance of the attached polymer wrap into the skin. In still another embodiment the needle can widen gradually as the distance away from the penetrating end increases, thereby gradually widening the point of penetration in the skin.

In one embodiment of the present invention, the polymer wrap will have sufficient rigidity and longitudinal strength to prevent buckling when entering the skin, while also possessing enough elasticity to allow administration of a formulation by passing through the polymer wrap. Examples of polymers that could be used to form the polymer wrap in embodiments of the invention include, but are not limited to, thermoplastics like polyethylene (PE), polypropylene (PP), polystyrene (PS), polytetrafluoroethylene (PTFE), and nylon. Other embodiments could also include polymers which are elastomers such as silicones, polyurethanes, nitrile rubbers, and polychlorprenes. In one embodiment, the hub is made of polycarbonate and is molded over the needle, and an elastomer is molded into or over the polycarbonate hub. In some embodiments the hub is detachable from the housing, while in other embodiments the hub is a part of the housing.

In one embodiment, the device comprises a 23-gauge needle. In other embodiments, suitable needle gauges could include needles of gauge 30 or smaller, when minimizing pain is particularly desirable. However, larger needles (e.g., as large as 21 gauge) may be included in some embodiments to further minimize needle clogging in those embodiments where formulation passes through the lumen of the needle. Generally, in certain embodiments of the invention include the smallest gauge needle possible for a given polymer wrap to maximize the cross sectional area between the needle and polymer, and to reduce trauma when penetrating the skin. Embodiments of the device can be used to administer fluids having a viscosity in the range from about 50 centipoise to about 90 centipoise. In one embodiment, the device comprises a 23-gauge needle for administering a fluid having a viscosity of about 70 centipoise.

Embodiments of the invention can be used to administer fluids into the skin in measured doses. In embodiments, volumetric markings can be incorporated into the housing to allow a user to measure how much drug formulation to administer into the skin. The volumetric markings can account for the volume of fluid carried by the channels of the hub in embodiments. In one embodiment, the fluid may comprise a drug formulation. In other embodiments, the fluid may include one or more microspheres. The microspheres may incorporate or comprise a drug formulation. In certain embodiments, the drug formulation may include, but is not limited to, a peptide or protein. Peptides can include, without limitation, any of: amylin, adrenomedullin ("ADM"), calcitonin ("CT"), calcitonin gene related peptide ("CGRP"), intermedin (e.g., AFP-6); cholecystokinin (a "CCK peptide", e.g., such as CCK-4, CCK-5, CCK-8, CCK-33), leptin, a pancreatic peptide ("PP"), peptide YY ("PYY"), and more generally, an incretin (e.g., glucagon-like peptide-1 ("GLP-1"), glucagon-like peptide 2 ("GLP-2"), exendin (e.g., exendin-3 or exendin-4), gastric inhibitory peptide (GIP)), oxyntomodulin (OXM), natriuretic peptides (e.g., ANP, BNP, CNP or urodilatin), a urocortin family peptide (e.g., Urocortin I, II, and III or Ucn-2 and -3), a neuromedin family peptide (e.g., neuromedin U or a splice variant thereof), secretin, gastrin releasing peptide/bombesin, ghrelin, a somatotropin, insulin, and combinations thereof. The sequence composition of the peptides can be as expressed in humans or can be species variants thereof, or can be analogs (agonist pr antagonist), derivatives, modified, chimeric and/or hybrid forms of these peptides. In certain aspects, a peptide can include functional domain(s) from one or more other peptides. For example, the peptide can include an amylin (or amylin analog) portion and a calcitonin (or calcitonin analog) portion in a single molecule wherein the amylin and calcitonin portion can be linked covalently via an amide bond or via a non-amide linkage. In one embodiment, the peptide is exenatide.

Additional embodiments of the present invention can be used for the injection of implants, slurries, gels, or similar types of solution into skin.

FIG. 1 is a cross-section of a device 100, according to one embodiment of the present invention. The device 100 includes a hub 101 that is connectable to, and may optionally include, a housing 102, which includes a chamber for receiving a fluid or formulation. In one embodiment the housing is a syringe, and the chamber for receiving a fluid or formulation is the barrel of the syringe. The hub may be connectable to the housing in any suitable manner known in art, including any suitable quick release connector, such as a threaded connection, or a permanent connection, such as molding the parts together during manufacturing, or a hub affixed to the housing by frictional forces. The device also includes a needle 103 and a polymer wrap 105. In one embodiment the polymer wrap is attached to the base of the hub 101 and tapered to the needle 103. Thus, when the skin is penetrated by the distal end of the needle the polymer wrap will also enter the skin.

Figure 2:
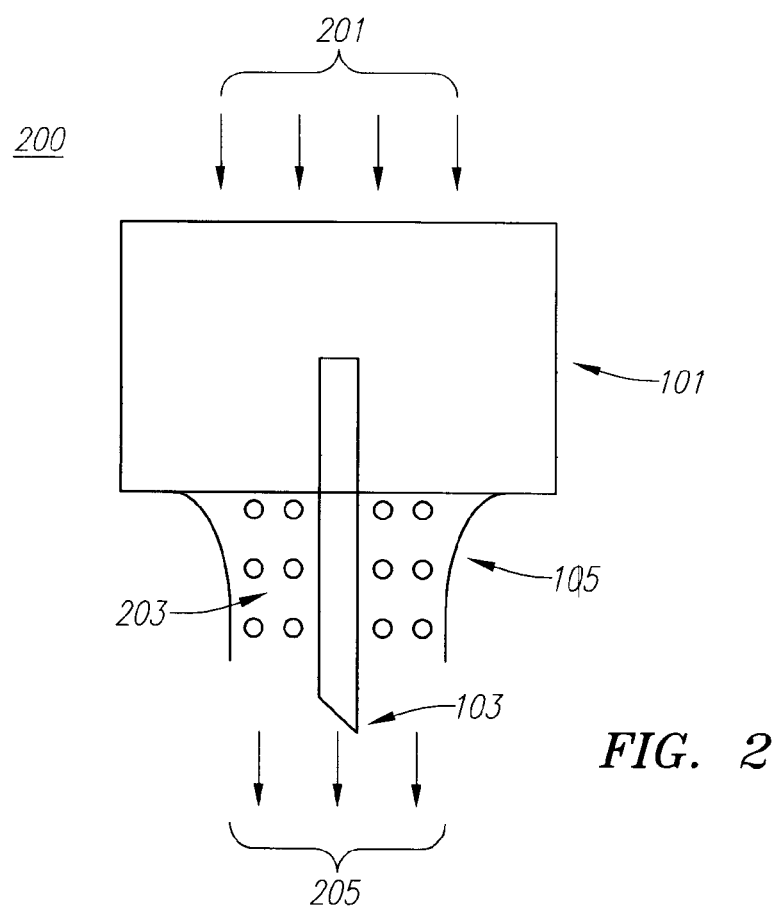
FIG. 2 exhibits the device according to one embodiment of the invention.

FIG. 2 illustrates a device 200, according to one embodiment of the present invention. The device 200 includes a hub 101. The device also includes a needle 103 and a polymer wrap 105. The polymer wrap 105 is attached to the base of the hub 101 and a space 203 is present between the polymer wrap and the needle 103. The hub 101, needle 103, and space 203 lie in a flow path of a fluid formulation 201. The fluid formulation passes through the hub 101, and the space 203 and exits through the distal end 205 of the polymer wrap.

Figure 3:
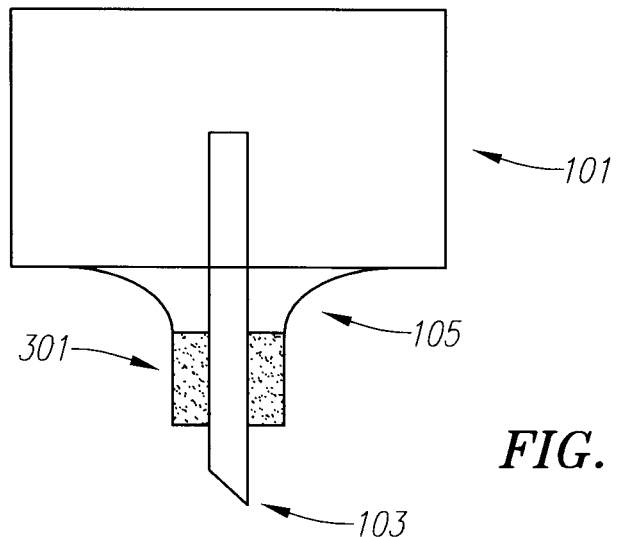
FIG. 3 exhibits the device according to one embodiment of the invention.

FIG. 3 is a diagram of a device 300 according to one embodiment of the invention. The device 300 includes a hub 101. The device also includes a needle 103 and a polymer wrap 105. The polymer wrap is attached to the base of the hub 101 and attached to the needle 103 with an adhesive 301.

Figure 4:
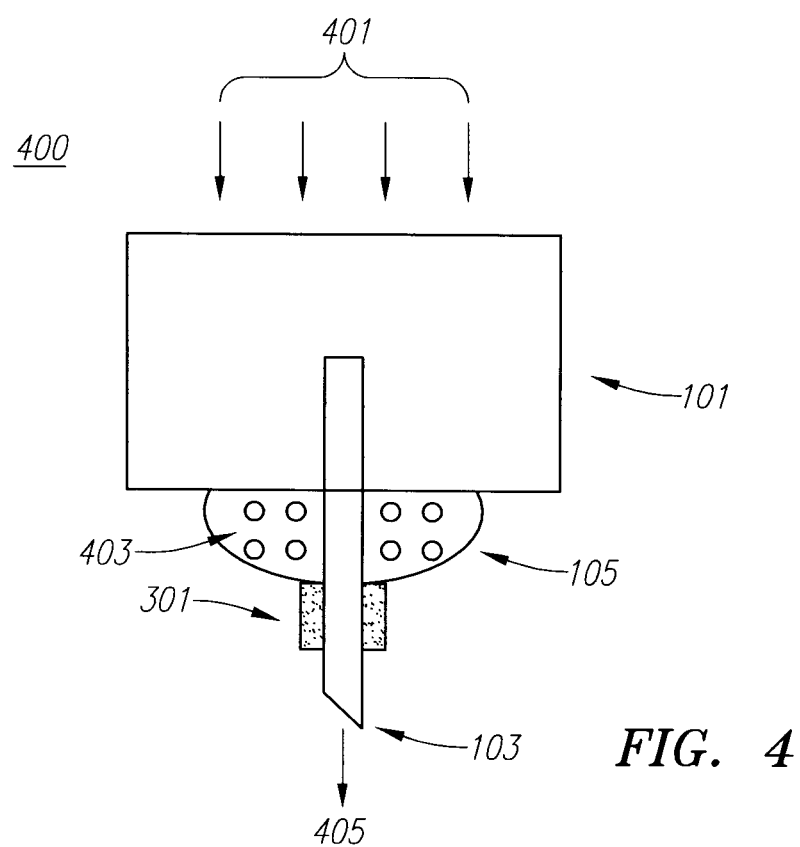
FIG. 4 exhibits the device according to one embodiment of the invention.

FIG. 4 is a diagram of a device 400 according to one embodiment of the present invention. The device 400 includes a hub 101. The device also includes a needle 103 and a polymer wrap 105. The polymer wrap 105 is attached to the base of the hub 101 and attached to the needle 103 by an adhesive 301. The hub 101, needle 103, and a space 403 between the polymer wrap 105 and needle 103 lie in a flow path of the fluid formulation 401. The space 403 expands as a fluid formulation 401 passes through the diameter of the hub and into the space 403. The fluid formulation 401 passes through the hub 101, the adhesive 301 between the needle 103 and polymer wrap 105 is broken, and in this embodiment the formulation 401 also passes through the needle 103, and exits as a formulation 405. The fluid formulation 401 also accumulates in the space 403, eventually causing the polymer wrap 105 to burst.

Figure 5:
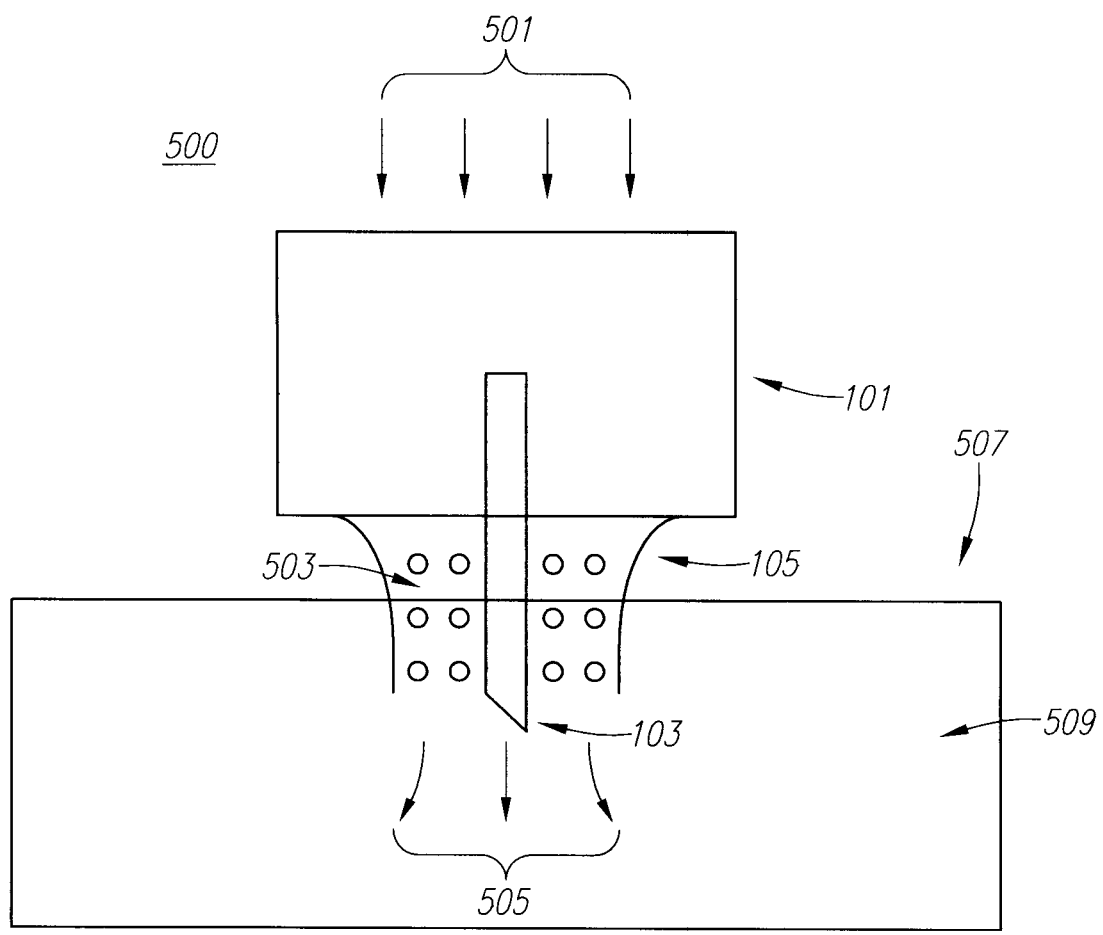
FIG. 5 illustrates a method of injecting a formulation into skin according to one embodiment of the invention.

FIG. 5 exhibits a method 500 injecting a fluid formulation 501 into a skin surface 507, according to one embodiment of the present invention. The device of the method 500 includes a hub 101, a needle 103 and a polymer wrap 105. The polymer wrap 105 is attached to the base of the hub 101 and a space 503 exists between the polymer wrap and the needle 103. The hub 101, needle 103, and space 503 lie in a flow path of a fluid formulation entering the hub 501. The needle 103 penetrates the skin surface 507 and enters below the skin surface 509. The fluid formulation 501 is pushed through the hub 101, the needle 103, and space 503, and exits as a formulation 505 in the below the skin surface 509.

EXAMPLE 1

A cavity mold with a core pin was used to mold a silicone sheath over a Luer fitting. The core pin was then removed and a trocar needle was inserted through the mold. Several different core pin shapes were used to test various tapers.

A 20 cc syringe and pressure gauge were attached to the luer/trocar needle assemble. Water was then passed through the assembly and the pressure was recorded. The prototype needle hub was pushed into a low durometer (30 A durometer) silicone "skin-like" material.

An internal core pin was utilized having a diameter of 0.200" that tapered down to a 0.016" silicon sheath diameter. Water passed through the device at about 25 psi. A pressure of 25 psi for injection corresponds to a plunger force of 2.5 pounds, which is within the acceptable level for plunger force.

Embodiments for practicing the present invention have been described. It will be understood and readily apparent to the skilled artisan that many changes and modifications may be made to the above-described embodiments without departing from the spirit and the scope of the present invention. The foregoing is illustrative only and that other embodiments may be employed without departing from the true scope of the invention defined in the following claims.

The invention claimed is:

1. A device for injecting a formulation, the device comprising:
   a needle having proximal and distal ends and a point to penetrate skin on the distal end;
   a hub having a diameter larger than that of the needle attached to the proximal end of the needle, wherein the hub is connected to a housing defining a chamber containing the formulation to be injected into the skin, and wherein the hub comprises a connector connecting the hub to the housing for receiving the formulation; and
   a polymer wrap enveloping the needle, a space being comprised between the needle and the polymer wrap;
   wherein the polymer wrap is tapered toward the needle along the direction toward the distal end of the polymer wrap and passes through the skin when the point is inserted into the skin,
   wherein the space between the needle and the polymer wrap lies in a flow path of the formulation that is injected through the space between the needle and the polymer wrap, the flow path extending between the needle and the polymer wrap through the distal end of the polymer, and
   wherein the housing comprises a syringe.

2. The device of claim 1 wherein the connector is selected from the group consisting of: a threaded connector and a quick release connector.

3. The device of claim 1 wherein the hub is connected to the housing by a molded connection.

4. The device of claim 1 wherein the diameter of the needle and at least a portion of the diameter of the hub lies in the flow path of the formulation into the skin.

5. The device of claim 1 wherein the needle is 30 gauge or smaller in diameter.

6. A device for injecting a formulation, the device comprising:
   a needle having, proximal and distal ends and a point to penetrate skin on the distal end;
   a hub having a diameter larger than that of the needle attached to the proximal end of the needle; and
   a polymer wrap enveloping the needle, a space being comprised between the needle and the polymer wrap;
   wherein the polymer wrap is tapered to the needle and passes through the skin when the point is inserted into the skin, and
   wherein the space between the needle and the polymer wrap lies in a flow path of the formulation that is injected through the space between the needle and the polymer wrap, and
   wherein the polymer wrap is attached to the needle by an adhesive.

7. The device of claim 1 wherein the polymer wrap comprises a polymer selected from the group consisting of polyethylene, polypropylene, polystyrene, polytetrafluoroethylene, nylon, polyurethane, nitrite rubber, and polychloroprene.

8. The device of claim 1 wherein the polymer wrap expands radially when the formulation is pushed through the space between the needle and the polymer wrap.

9. The device of claim 1 wherein an adhesive bond between the needle and the polymer wrap is broken when the formulation is pushed through the space between the needle and the polymer wrap.

10. A method for injecting a formulation into skin using a device comprising:
    a needle having proximal and distal ends and a point to penetrate skin on the distal end;
    a hub having a diameter larger than that of the needle attached to the proximal end of the needle; and
    a polymer wrap enveloping the needle, a space being comprised between the needle and the polymer wrap;
    wherein the polymer wrap is tapered to the needle and passes through the skin when the point is inserted into the skin, and
    wherein the space between the needle and the polymer wrap lies in a flow path of the formulation that is injected through the space between the needle and the polymer wrap,
    the method comprising;
    penetrating the skin with the point of the needle; and
    pushing the formulation through the device such that the formulation passes through the space between the needle and the polymer wrap.

11. The method of claim 10 wherein the hub of the device further comprises a connector for connecting the hub to a housing for receiving the formulation.

12. The method of claim 11 wherein the housing is a syringe, the syringe comprises a plunger, and the formulation is pushed through the device by applying pressure to the plunger.

13. The method of claim 12 wherein the formulation flows from the housing into the polymer wrap causing an adhesive bond between the needle and the polymer wrap to break, thus creating a flow path from the housing to the exterior of the device.

14. The method of claim 11 wherein the connector of the device is selected from the group consisting of: a threaded connector and a quick release connector.

15. The method of claim 10 wherein at least a portion of the polymer wrap is inserted into the skin when the point of the needle penetrates the skin.

16. The method of claim 14 wherein the polymer wrap expands radially when the formulation is pushed through the space between the needle and the polymer wrap.

17. The method of claim 10 wherein when penetrating the skin with the point of the needle, the polymer wrap is attached to the needle by an adhesive.

* * * * *